United States Patent [19]

Kaiser

[11] Patent Number: Plant 5,379

[45] Date of Patent: Dec. 25, 1984

[54] DISTINCT VARIETY OF STREPTOCARPUS NAMED FANTASIE

[75] Inventor: Herbert Kaiser, Rieskirchen, Fed. Rep. of Germany

[73] Assignee: Oglevee Associates, Inc., Connellsville, Pa.

[21] Appl. No.: 494,379

[22] Filed: May 13, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Webb, Burden, Robinson & Webb

[57] ABSTRACT

A new variety of Streptocarpus plant is characterized by its small, narrow and flattened leaves. The plant has bouquet-type flowers standing above the leaf line. The flowers have a flattened appearance resulting from flat bottom petals and reflexed top petals.

1 Drawing Figure

BACKGROUND OF THE NEW PLANT

The present invention comprises a new and distinct cultivar of *Streptocarpus* × *hybridus* known by the varietal name of Fantasie. The new cultivar is the product of a selective breeding program and is a hybridization of English hybrids of which the standard was a Streptocarpus known by the varietal name Kolibri. The new cultivar differs from the English hybrids in respect of color, early flowering, plant form and growth characteristics.

The new cultivar is generally characterized by its small, narrow and flattened leaves. The plant has bouquet-type flowers standing above the leaf line. The flowers have a flattened appearance resulting from flat bottom petals and reflexed top petals.

The new cultivar was discovered in 1979 in Reiskirchen, Federal Republic of Germany; was first asexually reproduced by cuttings in Reiskirchen, Federal Republic of Germany; and has been repeatedly asexually reproduced by cuttings at Oglevee Floral Company in Connellsville, Pa. It has been found to retain its distinctive characteristics through successive propagations.

The new cultivar, when grown in a greenhouse in Connellsville, Pa., has a response time of eight weeks from a well-rooted young plant in a 2¼ inch pot to a flowering plant in a 6 inch pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth the characteristics of the new cultivar. The data which define these characteristics were collected from asexual reproductions carried out by the Oglevee Floral Company in Connellsville, Pa. The plant history was taken on eight week plants blossomed under natural light in a greenhouse and color readings were taken indoors under 100 foot candles of cool white fluorescent light. Color references are to the R.H.S. Color Chart of The Royal Horticultural Society of London unless noted differently.

Botanical classification: Gesneriaceae (Family); *Streptocarpus* × *hybridus* (Genus × species).

Flower:

- *Fully expanded.*—5 To 6 centimeters.
- *Borne.*—In clusters of one to five flowers per flower stalk above the foliage. Flower stalk arises from mid-rib of each leaf.
- *Stem.*—Single, long, pubescent and round.
- *Form.*—Funnel formed in an umbel with upper two petals reflexed and lower petals flattened to give overall flat appearance.
- *Permanence.*—Long lasting 21 to 25 days.

Color:

- *Tonality from a distance.*—Amaranth 40 with amethyst 46 veining and mimosa 2 throat (Exotica III).
- *Front of petals.*—Fan 2 Red Purple Group 74A with veining Fan 12 Red Purple Group 71A from throat throughout petal but only on the bottom three petals.
- *Reverse of petals.*—Fan 2 Red Purple Group 74D.
- *Throat.*—Fan 1 Yellow Group 2C.
- *Discoloration.*—Insignificant.

Petals:

- *Texture.*—Satin.
- *Appearance.*—Individually lobed with slightly cuneate margins; top two petals reflexed and bottom three petals flat.
- *Arrangement.*—Regularly united into an elliptical form.
- *Persistence.*—21 To 25 days and remains on plant in dry form until picked.
- *Fragrance.*—None.

Reproductive organs:

- *Anthers.*—Two per flower, interconnected and imperfect; white with purple cast.
- *Filament.*—Attached to petals for a distance of 1.5 centimeters up from base and then free standing for 0.75 centimeter.
- *Pollen.*—Generally nonfertile.
- *Pistil.*—2 To 2.25 centimeters long.
- *Style.*—White with green cast; 0.5 centimeter long.
- *Stigma.*—White, flattened with reflexed tips.
- *Ovaries.*—1.5 Centimeters long and 2 millimeters wide; purple cast.

Plant:

*Form.*—Leaves rosette from a crown at the soil line.

*Growth.*—A spreading, free flowing habit with leaves being elliptical.

*Height from soil line.*—5 To 10 centimeters.

*Spread.*—35 To 45 centimeters.

Foliage:

*Size.*—10 To 20 centimeters in length; 4 to 7 centimeters wide at widest point.

*Quantity.*—8 To 12 leaves.

*Shape.*—Elliptical.

*Top side.*—Fan 3 Green Group 137A.

*Under side.*—Fan 3 Green Group 138D.

*Ribs and veins.*—Pinnate.

*Rib and vein color.*—Fan 3 Green Group 138D.

*Margin.*—Cuneate.

*Leaf tips.*—Obtuse.

*Leaf base.*—Acute.

I claim:

1. A new and distinct variety of Streptocarpus, substantially as herein shown and described.

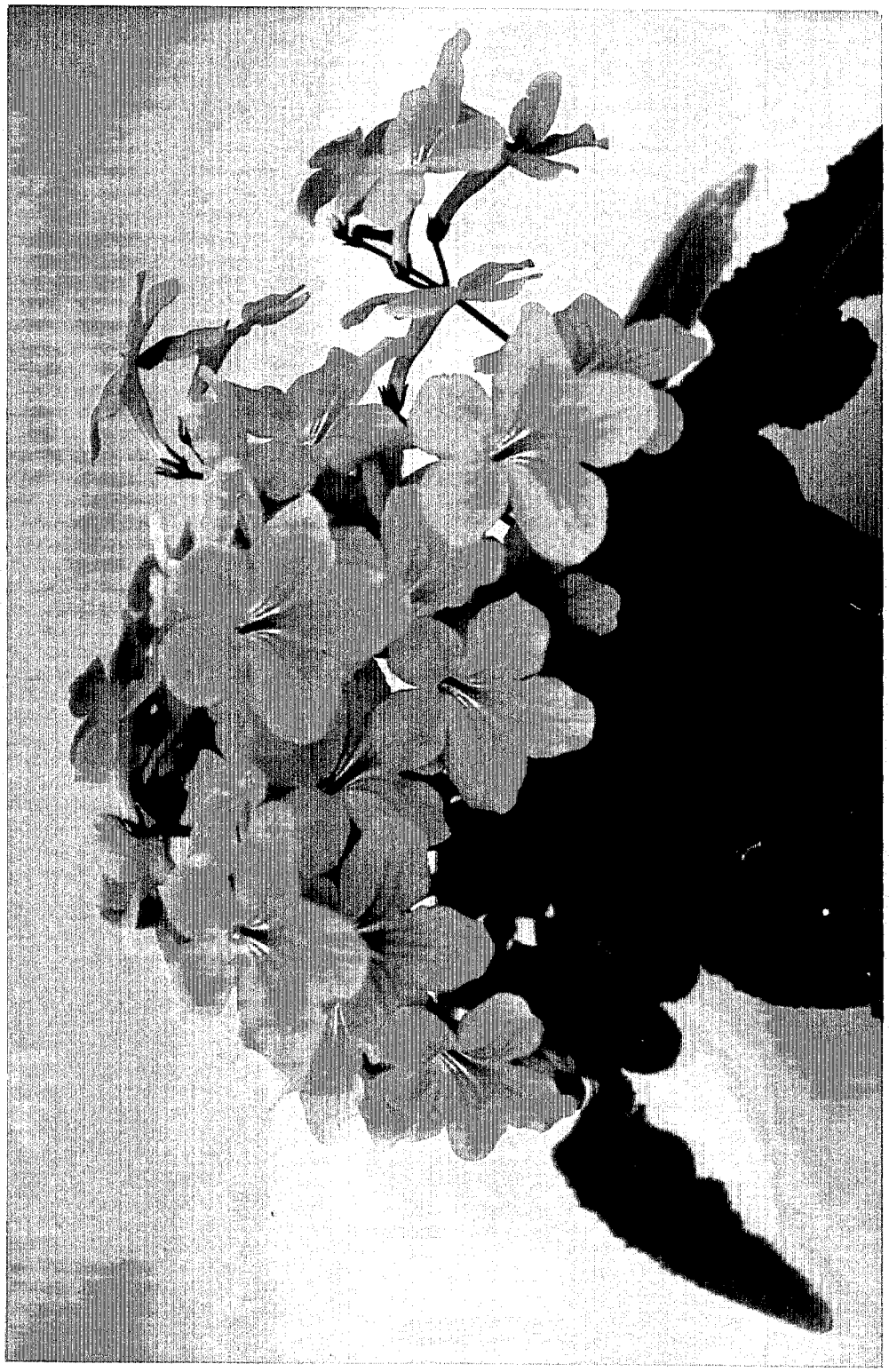

* * * * *